United States Patent [19]

Matsuda et al.

[11] Patent Number: 5,202,227
[45] Date of Patent: Apr. 13, 1993

[54] CONTROL OF CELL ARRANGEMENT

[75] Inventors: Takehisa Matsuda, Minoo; Kazuhiko Inoue, Kobe; Nobutaka Tani, Osaka, all of Japan

[73] Assignee: Kanegafuchi Kagaku Kogyo Kabushiki Kaisha, Osaka, Japan

[21] Appl. No.: 531,596

[22] Filed: Jun. 1, 1990

[30] Foreign Application Priority Data

Jun. 3, 1989 [JP] Japan .................................. 1-141964
Jun. 3, 1989 [JP] Japan .................................. 1-141965

[51] Int. Cl.$^5$ ...................... G03F 7/008; G03F 7/00
[52] U.S. Cl. .................................. 430/320; 430/167;
430/195; 430/197; 430/270; 435/240.23;
435/230.243; 435/284; 435/285
[58] Field of Search ............... 430/320, 270, 167, 195,
430/197; 435/284, 285, 240.23, 240.243

[56] References Cited

U.S. PATENT DOCUMENTS

| 3,721,566 | 3/1973 | Laridon et al. | 430/270 |
| 3,854,946 | 12/1974 | Sayigh et al. | 430/270 |
| 4,099,973 | 7/1978 | Miura et al. | 430/270 |
| 4,229,514 | 10/1980 | Kurita et al. | 430/270 |
| 4,832,759 | 5/1989 | Curtis et al. | 435/285 |

FOREIGN PATENT DOCUMENTS

| 0145406 | 6/1985 | European Pat. Off. | |
| 2-084174 | 3/1990 | Japan | 435/284 |

OTHER PUBLICATIONS

Patent Abstracts of Japan, vol. 13, No. 399 (C-632) (3747) Sep. 5, 1989.
Photographic Science and Engineering, vol. 17, No. 5 Sep./Oct. 1973 F. A. Stuber et al.
W. S. DeForest, "Photoresist: Materials and Processes", 1975, pp. 37-41.
Biomaterials, vol. 10, No. 2, Mar., 1989, pp. 85-90 C. Klein-Soyer et al.

Primary Examiner—Marion E. McCamish
Assistant Examiner—Janis L. Dote
Attorney, Agent, or Firm—Armstrong, Westerman, Hattori, McLeland & Naughton

[57] ABSTRACT

A device for controlling cell arrangement having a pattern composed of a cell adhesive surface and a cell non-adhesive surface, which has a good selectivity of cell adhesion and which can provide a fine pattern of cells in high resolution by culturing cells in a usual manner. The device is prepared by a process which comprises applying a photosensitive, cell adhesive or cell non-adhesive polymer to a surface having a reverse cell adhesivity property to that of the applied polymer, and patternwise irradiating a light to the photosensitive polymer layer followed by development; a process which comprises patternwise irradiating UV or radiation to a cell non-adhesive surface to produce a cell adhesive functional group such as carboxyl group or amino group in the irradiated portion; or a process which comprises patternwise irradiating UV or radiation to a cell adhesive or non-adhesive surface made of plastics to produce a polymerization initiation site in the irradiated portion, and graft-polymerizing at least one monomer having the reverse cell adhesivity property to the plastic surface to produce a polymer on the irradiated portion of plastic surface.

3 Claims, 3 Drawing Sheets

CONTROL OF CELL ARRANGEMENT

BACKGROUND OF THE INVENTION

The present invention relates of control of the arrangement of cells, and more particularly to a device for controlling cell arrangement, a process for preparing the device and a process for controlling the cell arrangement.

In recent years, with rapid progress of cell technology, technology in manufacturing an LSI and medical technology, attention is attracted on devices using cells, such as ultra-small biosensor, switching device, bioreactor, hybrid type artificial organs and neuro-computer, and development of them has been lively made.

It has been difficult to arrange cells as desired and keeping the functions thereof, and the difficulty is one of obstacles to realization of devices using cells. The cell arrangement control technique for arranging the cells as desired, for instance, in a circuit network would become a key technology for realizing these devices.

It has been attempted to control cell arrangement by patternwise applying fibronectin which is a cell adhesive protein, using an ink jet printer, and culturing cells on the protein pattern. However, this process is poor in resolution and uniformity and is not suitable for fine processing. Recently, control of direction of neuron cell synapse growth is attempted using an artificial uneven surface, but formation of a desirable arrangement is not achieved.

It is a primary object of the present invention to provide a technique for easily controlling the arrangement of cells.

The above and other objects of the present invention will become apparent from the description hereinafter.

SUMMARY OF THE INVENTION

It has now been found that arrangement of cells can be easily controlled by culturing cells on a material having a pattern composed of a cell adhesive surface and a cell non-adhesive surface, whereby a desirable cell pattern can be easily obtained, and that a device having a pattern for cell arrangement composed of the cell adhesive surface and the cell non-adhesive surface, which is suitable for use in formation of a cell pattern, can be easily prepared through specific steps.

In an aspect of the present invention, there is provided a device for controlling cell arrangement having a pattern composed of a cell adhesive surface and a cell non-adhesive surface. When cells are cultured on the device, cells grow only on the cell adhesive surface, thus a pattern of cells is obtained.

The patterned cell adhesive surface can be easily obtained by utilizing a photosensitive polymer having a cell adhesivity or a cell non-adhesivity. Accordingly, in another aspect of the present invention, there is provided a process for preparing a cell arrangement control device which comprises applying, onto a surface having either a cell adhesivity or a cell non-adhesivity, a photosensitive polymer having the reverse property to said surface with respect to the cell adhesivity characteristic, irradiating the resulting photosensitive polymer layer patternwise with a light, developing the irradiated layer to form a pattern in the polymer layer so that the cell adhesive or non-adhesive surface appears in the non-irradiated portion.

Patternwise irradiation of a cell adhesive or non-adhesive surface with ultraviolet rays or radiation is also effective for forming the patterned cell adhesive surface.

Accordingly, in another aspect of the present invention, the cell arrangement control device is prepared by patternwise irradiating a cell non-adhesive surface with ultraviolet rays or radiation, thereby introducing a functional group having a cell adhesivity to the irradiated portion of the cell non-adhesive surface.

In still another aspect of the present invention, the cell arrangement control device is prepared by patternwise irradiating a cell adhesive or non-adhesive surface with ultraviolet rays or radiation, thereby introducing polymerization initiation sites to the irradiated portion, and graft-polymerizing a monomer or monomers capable of providing a polymer having a cell adhesivity or a cell non-adhesivity onto the irradiated portion, thereby forming a pattern of the polymer.

It is possible to provide a fine pattern of cells in high resolution. Also since, according to the above processes, the patterned upper layer of the device is firmly fixed to the surface of the under layer by chemical bonding or a latent pattern is formed in a cell non-adhesive surface, the patterned layer does not peel off during rinsing or culture of cells and the accuracy of the pattern is maintained.

Controlled cell arrangement, namely a patterned cell layer, is easily obtained by culturing cells on the thus obtained cell arrangement control devices.

DETAILED DESCRIPTION

Figure 1:
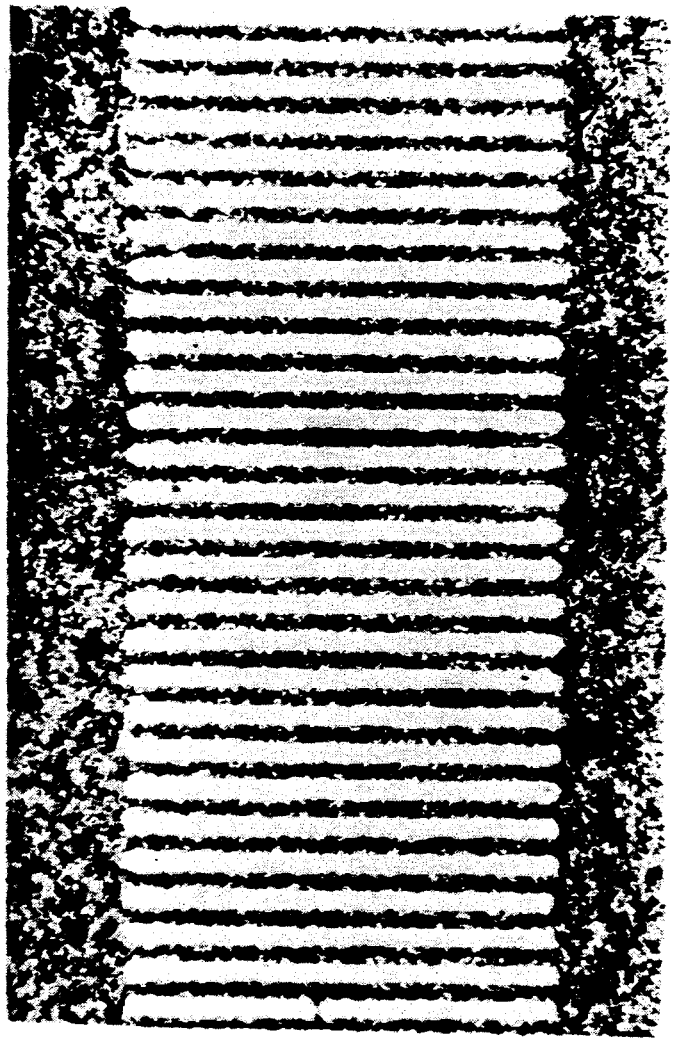
FIG. 1 is a microphotograph showing a pattern of stained cells.

In the cell arrangement control device of the present invention, a pattern composed of a cell adhesive surface and a cell non-adhesive surface is formed in or on the surface of a basis material constituting the device of the present invention (the device-constituting material being hereinafter referred to as "substrate").

Examples of the material for the substrate are, for instance, various plastics, glass, metals and ceramics, which may be in any form such as film, sheet, plate, dish, tube and other desired forms. Articles used already as devices or for other purposes, e.g. incubation dish and semiconductor plate or board, can also be used in the present invention.

The cell adhesive surface includes, for instance, a surface having a charged functional group, e.g. carboxyl group or amino group, and/or a cell adhesive peptide, e.g. RGDS (Arg-Gly-Asp-Ser), and a surface to which a high molecular weight compound having a cell adhesivity (hereinafter referred to as "cell adhesive polymer") is fixed.

Examples of the cell adhesive polymer which provides the cell adhesive surface are, for instance, a synthetic polymer having electric charge such as polyacrylic acid, polyvinyl sulfuric acid, polystyrene sulfonic acid or polyallylamine; a polysaccharide having electric charge such as chondroitin sulfate, dermatan sulfate, dextran sulfate, keratan sulfate, heparane sulfate, hyaluronic acid or chitin; a cell adhesive protein such as collagen, gelatin, fibronectin or hydronectin; a cell adhesive protein-fixed synthetic polymer, a cell adhesive peptide-fixed synthetic polymer, and other materials having a cell adhesivity. The cell adhesive polymers may be used alone or in admixture thereof.

The surface having the functional group and/or cell adhesive peptide is formed in the surface of the substrate or on the surface of the substrate. That is to say, the functional group and/or peptide may be introduced directly into the surface of the substrate or may be introduced by fixing a high molecular weight compound having functional group or peptide onto the surface of the substrate.

The direct introduction of the functional group such as carboxyl group or amino group can be conducted in a known manner, for instance, by exposing the surface of the substrate made of plastics in a desired form such as dish, film or tube to ultraviolet rays in air or to radiation such as plasma, electron beams or γ-rays.

The fixing of the high molecular weight compound having functional group and/or peptide to the substrate can be made by various processes, for instance, a process wherein the functional group of the substrate and the functional group of the high molecular weight compound are combined by chemical reaction, a process wherein a monomer having a functional group with electric charge such as carboxyl group is graft-polymerized onto the surface of the substrate, a process wherein a monomer is graft-polymerized onto the surface of the substrate, and carboxyl group or amino group is introduced to the graft-polymerized polymer, for instance, by graft-polymerizing acrylamide onto the substrate surface, and hydrolyzing the amide to carboxyl group by means of alkali treatment or converting the amide to amino group by means of treating with an alkali solution of sodium hypochlorite (Hofmann degradation).

The cell non-adhesive surface includes a hydrophobic surface having a contact angle of at least 90°, and a hydrophilic surface having no electric charge and having a contact angle of at most 50°.

Examples of the hydrophobic surface are, for instance, surfaces of polytetrafluoroethylene and silicone.

Representative materials which provide the hydrophilic surface having a contact angle of at most 50° are hydrophilic polymers having no electric charge. Examples of the hydrophilic polymer are, for instance, polyvinyl alcohol, polyethylene glycol, polyacrylamide, polydimethylacrylamide, polyhydroxyethyl methacrylate, copolymers prepared from monomers constituting the preceding hydrophilic polymers, and cellulose.

The hydrophobic surface and hydrophilic surface applicable to the present invention are not limited to those exemplified above.

The cell non-adhesive surface can be provided to the substrate, for instance, by coating, laminating, photochemical fixing and other appropriate processes. It is also possible to provide the cell non-adhesive surface to the substrate by graft-polymerizing a monomer which is hydrophilic and has no electric charge to produce the cell non-adhesive polymers as mentioned above.

When the substrate itself is made of the above-mentioned hydrophobic or hydrophilic material, it is not necessary to provide the cell non-adhesive surface to the substrate.

The cell arrangement control device of the present invention can be prepared by processes utilizing a photosensitive hydrophilic polymer or by processes wherein patternwise irradiation of a cell adhesive or non-adhesive surface is conducted in order to produce functional groups or radicals.

In the first embodiment of the present invention, the cell arrangement control device is prepared by a process which comprises (1) forming a layer of a photosensitive polymer having a cell non-adhesivity on a cell adhesive surface by coating or causing to adsorb the photosensitive hydrophilic polymer, (2) placing a photomask having a desired pattern on the photosensitive cell non-adhesive polymer layer and exposing to a light, and (3) developing the pattern by rinsing the photosensitive cell non-adhesive polymer layer to form a pattern of the cell non-adhesive polymer on the cell adhesive surface.

The photosensitive polymer having cell non-adhesivity used in the present invention can be a cell non-adhesive hydrophilic polymer to which a photosensitive group is directly introduced, or a photosensitive composition containing a cell non-adhesive hydrophilic polymer and a photosensitive compound. For instance, in the above process, the cell non-adhesive hydrophilic polymer, preferably the above-mentioned hydrophilic polymer having no electric charge, can be easily fixed patternwise on the cell adhesive surface, for instance, by forming a layer of a composition containing the cell non-adhesive hydrophilic polymer and a compound having at least two azido groups on the cell adhesive surface formed in or on the substrate, and patternwise irradiating a light. Cell non-adhesive hydrophilic polymers to which at least one azido group is directly introduced can be used, but the use of the composition containing the hydrophilic polymer and the azido compound is preferred, since no special procedure for introducing azido groups to the polymer is required and the removal of non-reacted substances is easy upon the development. It is preferable to use the azido compound in an amount of at least 1% by weight based on the polymer.

As the compound having at least two azido groups, there can be used, for instance, usual bisazido compounds as shown in Table 1 and azido-containing polymers wherein at least two azido groups are introduced into one molecule of the polymers. However, the compound having at least two azido groups used in the present invention is not limited to them. The azido group includes, for instance, carbonylazido group (—CON₃), sulfonylazido group (—SO₂N₃) and the aromatic azido group

Above all, the aromatic azido group and sulfonylazido group are preferable because of the good stability. Particularly, a compound having aromatic azido group having an electron attractive substituent such as nitro group and a bisazido compound photosensitive against i-line or g-line are preferable in respect that they can be converted into nitrene by irradiation with a light having a relatively longer wave length (>320 nm).

TABLE 1
| Bisazido compound | Photosensible range |
|---|---|
| 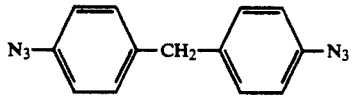 | deep UV |
| 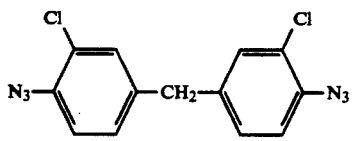 | " |
| 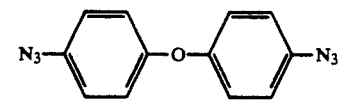 | " |
| 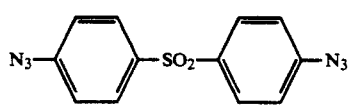 | " |
| 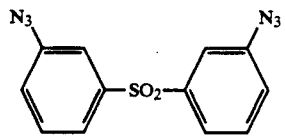 | " |
| 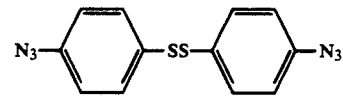 | " |
| 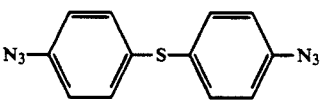 | " |
| 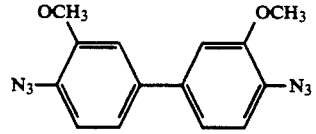 | i-line |
| 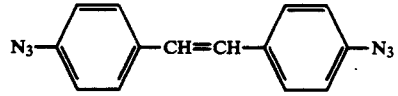 | i-line |
| 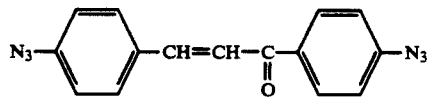 | " |
| 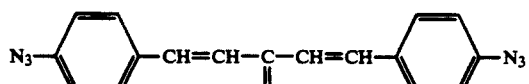 | " |
| 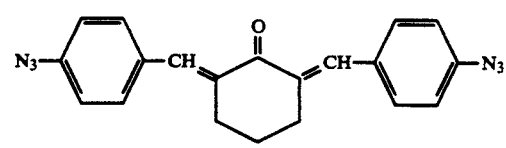 | " |

TABLE 1-continued

| Bisazido compound | Photosensible range |
|---|---|
| (structure: N₃-C₆H₄-CH=C(cyclohexanone with CH₃)=CH-C₆H₄-N₃) | " |
| (structure: N₃-C₆H₄(SO₃Na)-CH=CH-C₆H₄(NaO₃S)-N₃) | " |
| (structure: N₃-C₆H₄-CH=CH-CH=C(cyclohexanone with t-Bu)=CH-CH=CH-C₆H₄-N₃) | g-line |

The cell non-adhesive hydrophilic polymer is fixed to the cell adhesive surface through the azido compound by a reaction wherein the azido groups are converted into nitrene groups by light irradiation and the nitrene groups undergo chemical reactions as shown by the following reaction formulas with the cell adhesive surface and the hydrophilic polymer, namely a hydrogen-abstraction reaction represented by the formula (1), an insertion into C—H bond or an addition to double bond represented by the formula (2) and coupling reaction represented by the formula (3).

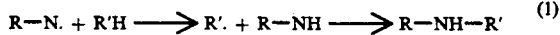

(1) R—N. + R'H ⟶ R'. + R—NH ⟶ R—NH—R'

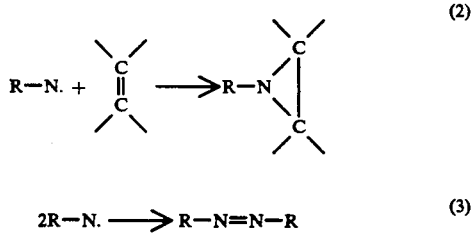

(2)

(3) 2R—N. ⟶ R—N=N—R

The nitrene group is so highly reactive that bonding may be formed through other reactions than those above-mentioned. Also the above-mentioned reactions may occur between the hydrophilic polymer molecules to cause crosslinking. There is a case where the cell non-adhesive polymer is more stably fixed to the cell adhesive surface by occurrence of crosslinking.

It is not always required that the cell non-adhesive hydrophilic polymer is fixed to the cell adhesive surface by chemical bonding as mentioned above, but it may be adhered as a film onto the cell adhesive surface.

The application of the photosensitive composition to the cell adhesive surface can be made, for instance, by a method wherein the photosensitive composition is dissolved or dispersed in a volatile organic solvent such as methanol, the solution or dispersion is coated by spreading or spraying onto the cell adhesive surface and it is dried to form a thin layer of the composition on the cell adhesive surface, or a method wherein the cell adhesive surface is brought into contact with an aqueous solution or colloidal solution of the photosensitive composition so as to adsorb the composition, for instance, by immersion in the solution of by causing the solution to flow on the cell adhesive surface. The film formation by casting from the solution in a volatile organic solvent such as methanol is preferred because a uniform thin layer is easily obtained.

Also, there may be usable a method wherein the compound having at least two azido groups is applied onto the cell adhesive surface and the cell non-adhesive hydrophilic polymer is then applied.

As a light source for the irradiation operation, there can be used various kinds of mercury light such as a high pressure mercury lamp, a low pressure mercury lamp, an extra-high pressure mercury lamp; excimer laser; and the like. In case of using azido compounds sensitive to the longer wavelength region in the ultraviolet region, damages by the shorter wavelength ultraviolet rays to the hydrophilic polymer, the cell adhesive surface or the device material can be reduced by cutting off the shorter wavelength region using a filter. This method is particularly preferable in case that hydrophilic polymers such as protein are used.

The reaction of a nitrene group is accomplished in a very short time, and irradiation for five minutes is enough for the reaction.

The patternwise irradiation can be made by various methods, for instance, a method wherein a light is irradiated through a photomask having a pattern placed on the photosensitive layer, or a method utilizing lithography by means of excimer laser.

In the second embodiment of the present invention, the cell arrangement control device is prepared in the same manner as above except that instead of forming the layer of the photosensitive cell non-adhesive polymer on the cell adhesive layer in the step (1), a layer of a photosensitive polymer having cell adhesivity is formed on a cell non-adhesive surface by coating or causing to adsorb the photosensitive polymer. As the photosensitive polymer, there can be used the cell adhesive polymers mentioned above to which at least one azido group is directly introduced or a photosensitive composition containing the above-mentioned cell adhesive polymers and the above-mentioned azido compounds having at least two azido groups. For instance, the cell adhesive hydrophilic polymer can be easily fixed patternwise onto the cell non-adhesive surface by applying the photosensitive composition to the cell non-adhesive surface formed on the substrate, and patternwise irradiating a light such as ultraviolet rays.

According to the above-mentioned first and second processes of the present invention, the patterned upper layer is covalently bonded through nitrogen atom derived from azido group to the cell adhesive or non-adhesive surface of the under layer, thus the pattern is firmly fixed to the under layer.

The cell arrangement control device can also be prepared by a process utilizing irradiation of ultraviolet rays or radiation wherein a functional group which renders a surface cell-adhesive, or a site capable of initiating a polymerization is formed in a cell adhesive or non-adhesive surface by patternwise irradiation of ultraviolet rays or radiation.

In the third embodiment of the present invention, the device is prepared by a process which comprises placing a mask having a desired pattern on the cell non-adhesive surface of the substrate, and irradiating ultraviolet rays or radiation to the cell non-adhesive surface through the mask, thereby producing a cell adhesive functional group only in the exposed portion of the cell non-adhesive surface to patternwise form a cell adhesive surface in the cell non-adhesive surface.

The cell adhesive functional groups formed in this process to patternwise render the cell non-adhesive surface cell-adhesive are carboxyl group and amino group. As the cell non-adhesive surface used in this process, there are used hydrophilic polymers having no electric charge and capable of producing carboxyl group or amino group, e.g. polydimethylacrylamide, among the hydrophilic polymers exemplified before.

The formation of the functional group can be conducted in a known manner, for instance, by irradiation of ultraviolet rays in the air or treatment with radiation. Examples of the radiation are, for instance, plasma obtained by corona discharge or glow discharge, electron beams, γ-rays, and other high energy rays. The use of the plasma obtained by glow discharge is preferred in view of its applicability to various materials and the effect, and $N_2$ plasma and $O_2$ plasma are particularly preferred in view of efficiency in producing the functional groups. The use of ultraviolet rays is also preferable in that the treatment in high degree of resolution is possible.

The masks used in the invention are those having an opening corresponding to a pattern to be delineated and capable of causing only the portion corresponding to the opening to expose to ultraviolet rays or radiation irradiated, and general photomasks can be utilized. Particularly, in case of using radiation such as plasma, a mask made of a non-metallic material is preferable, since the use of a metallic mask may be inferior in degree of resolution owing to discharge from the mask.

In the fourth embodiment of the present invention, the cell arrangement control device is prepared by a process which comprises placing a mask having a desired pattern on a cell adhesive or non-adhesive surface of the substrate, irradiating ultraviolet rays or radiation to the surface through the mask, thereby producing a polymerization initiation site only in the exposed portion, and graft-polymerizing a cell adhesive or non-adhesive monomer on the treated surface, thereby producing the polymer only on the exposed portion in the form of the pattern.

The polymerization initiation site induced by the irradiation in this process is a polymer radical derived from the material of the substrate itself or the polymer layer provided on the substrate. The polymer radical can be induced in a known manner by treatment with ultraviolet rays or radiation such as plasma. Since UV treatment generally requires the use of sensitizers, the radiation treatment which does not require the use of sensitizers is preferred.

The radiations mentioned above can be used in this process. Above all, plasma as obtained by glow discharge is preferable.

The graft polymerization of cell adhesive monomers or cell non-adhesive monomers based on the thus induced radicals can be conducted, for instance, by directly introducing the monomers into the system where the radicals are produced, or by once bringing the radicals into contact with air to convert into peroxide, adding the monomers to a polymerization system, and decomposing the peroxide into radicals to initiate the polymerization.

Examples of the cell adhesive monomer are, for instance, monomers having electric charge such as acrylic acid, styrene sulfonic acid and vinyl sulfonic acid. Examples of the cell non-adhesive monomer are, for instance, hydrophilic monomers having no electric charge such as acrylamide, dimethylacrylamide, ethylene glycol and hydroxyethyl methacrylate.

The photomasks mentioned above are also applicable to this process.

The arrangement of cells can be easily controlled by a cell culture in a usual manner using the cell arrangement control devices prepared as mentioned above. It is possible to form a fine pattern of cells of a high resolution on the order of up to μm.

The obtained fine patterns are useful for the production of ultra-small biosensor, switching device, bioreactor, hybrid type artificial organ and so on, and the development of neuro-computer. The devices are also applicable to research of cell functions such as information transmission between cells.

The present invention is more specifically described and explained by means of the following examples, in which all parts and % are by weight unless otherwise noted. It is to be understood that the present invention is not limited to these examples.

EXAMPLE 1

N,N-Dimethylacrylamide was polymerized in acetone in the presence of a redox catalyst system of benzoyl peroxide and N,N-dimethyl-p-toluidine to produce poly(N,N-dimethylacrylamide)(hereinafter referred to as "PDMAA").

A mixture of 95 parts of PDMAA and 5 parts of sodium 4,4'-diazidostilbene-2,2'-disulfonate as the bisazido compound was dissolved in methanol to form a 0.1% solution.

Figure 3:
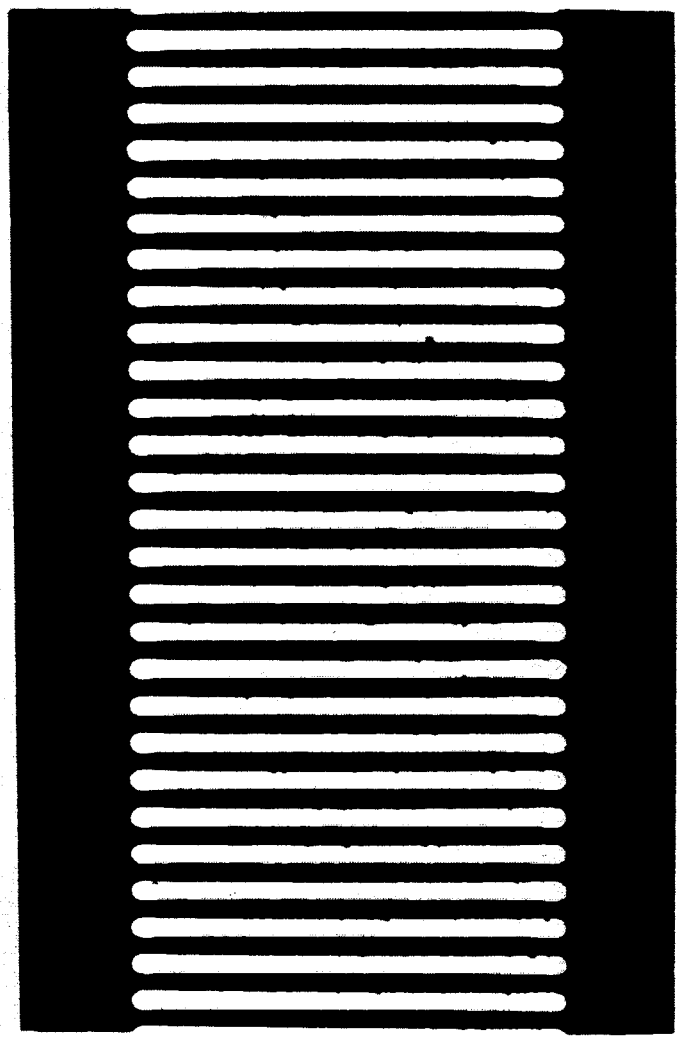
FIG. 3 is an enlarged photograph of a photomask in the same enlargement ratio as that of the photograph of FIG. 1.

The obtained solution was cast onto a polystyrene dish for tissue culture and dried to form a film having a thickness of several tens of nm. On the thus formed film was placed a photomask as shown in FIG. 3 having slits wherein the width of a pair of the opening portion and the non-opening portion was 250 μm, and the film was exposed through the photomask to a light from a high pressure mercury lamp (400 W) for 30 seconds (corresponding to light quality of about 600 mJ/cm² measured by a detector for i-line 365 nm).

The exposed film was then developed by thoroughly rinsing with methanol and water to remove the non-exposed portion of PDMAA film, thus the dish having a fine pattern composed of PDMAA and the dish surface.

Figure 2:
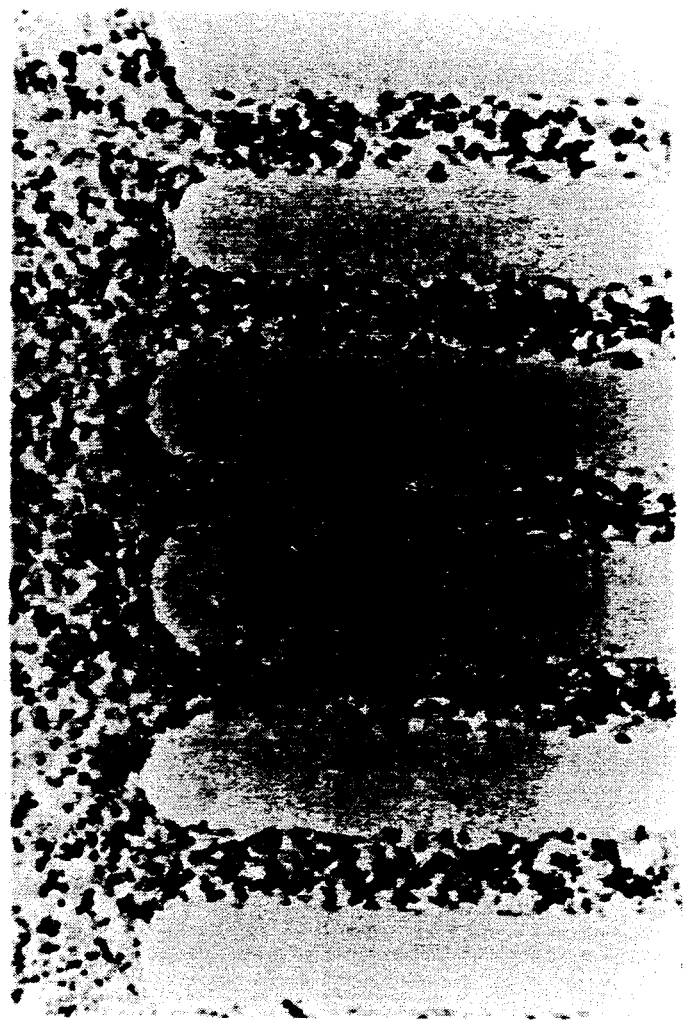
FIG. 2 is a further enlarged microphotograph of the pattern shown in FIG. 1.

By using DMEM (Dulbecco's Modified Eagle's Medium) containing fetal calf serum as a culture medium, bovine vascular endothelial cells were inoculated into the thus obtained dish, and cultured in a $CO_2$ incubator at 37° C. The endothelial cells selectively spread and grew only on the PDMAA-removed portion (non-exposed portion), thus the cell pattern shown in FIGS. 1 and 2 was obtained, wherein FIG. 1 was a photograph of the pattern of the stained cells (enlargement ratio being the same as FIG. 3) and FIG. 2 was a photograph of further enlarged pattern shown in FIG. 1.

EXAMPLE 2

A 0.1% methanol solution of PDMAA and the bisazido compound prepared in the same manner was cast on a polystyrene dish and dried to form a thin film. The PDMAA film was irradiated with ultraviolet rays from a high pressure mercury lamp to fix the film onto the surface of the dish.

A copolymer of 80% of N,N-dimethylacrylamide and 20% of acryloyloxysuccinimide was reacted with fibronectin in a phosphate buffer (pH 8.5) to produce a fibronectin-fixed N,N-dimethylacrylamide copolymer (hereinafter referred to as "FN-PDMAA").

A mixture of 95 parts of FN-PDMAA and 5 parts of sodium 4,4'-diazidostilben-2,2'-disulfonate was dissolved in methanol to give a 0.1% solution. The resulting solution was cast on the PDMAA-fixed dish and dried to form a FN-PDMAA film having a thickness of several tens of nm. The FN-PDMAA film containing bisazido compound was then exposed through a photomask to ultraviolet rays from a high pressure mercury lamp for 30 seconds.

The exposed film was then developed by thoroughly rinsing with methanol and water to remove the masked portion of the FN-PDMAA film, thus obtaining a dish having a fine pattern composed of the FN-PDMAA and the PDMAA surface.

Bovine vascular endothelial cells were cultured in the same manner as in Example 1 by using the thus obtained dish. The cells selectively spread and grew only on the FN-PDMAA fixed portion (exposed portion) to give a cell pattern.

EXAMPLE 3

A 0.1% methanol solution of 95 parts of PDMAA and 5 parts of sodium 4,4'-diazidostilbene-2,2'-disulfonate was cast on a polystyrene Schale and dried to give a PDMAA film containing the bisazido compound. The PDMAA film was then irradiated with ultraviolet rays from a high pressure mercury lamp to chemically fix PDMAA onto the surface of the Schale.

The same photomask as used in Example 1 was placed on the PDMAA film. The PDMAA film covered with the photomask was subjected to glow discharge treatment in an ion coater (IB-3 type ion coater made by Eiko Engineering Co., Ltd.) (0.2 Torr, 5 mA × 10 seconds), and was then allowed to stand in contact with air to produce carboxyl group in the exposed portion of the PDMAA film.

Bovine vascular endothelial cells were cultured on the thus obtained Schale in the same manner as in Example 1. The cells selectively grew only on the carboxyl group introduced portion (exposed portion).

EXAMPLE 4

A PDMAA-fixed Schale prepared in the same manner as in Example 3 was irradiated in air with ultraviolet rays from a low pressure mercury lamp for 1 hour through the photomask shown in FIG. 3 to induce carboxyl group in the exposed portion of the PDMAA film.

Bovine vascular endothelial cells were cultured on the thus treated Schale in the same manner as in Example 1. The cells selectively grew only on the carboxyl group-introduced portion (exposed portion) to give a cell pattern.

EXAMPLE 5

A polystyrene Schale for tissue culture use was covered with the photomask shown in FIG. 3, subjected to the glow discharge treatment in an ion coater and then brought into contact with air in order to introduce peroxide into the exposed portion of the polystyrene Schale.

The Schale was then immersed in a 5% aqueous solution of acrylamide, and after thoroughly degasing, the system was sealed and the polymerization of acrylamide was conducted at 60° C. for 2 hours. After the completion of the polymerization, the Schale was washed well with water to give a tissue culture polystyrene Schale having polyacrylamide grafted only onto the exposed portion of the Schale.

The culture of cells was carried out on the thus obtained Schale in the same manner as in Example 1. The cells selectively grew only on the non-grafted portion (non-exposed portion), thus the same cell pattern as that shown in FIGS. 1 and 2 was obtained.

EXAMPLE 6

The mask shown in FIG. 3 was placed on a polytetrafluoroethylene film, and the film was subjected to glow discharge treatment in the same manner as in Example 3 to introduce peroxide into the exposed portion of the film. Acrylamide was then graft-polymerized only onto the exposed portion in the same manner as in Example 5.

The thus obtained polyacrylamide-grafted polytetrafluoroethylene film was immersed in a 1N-NaOH aqueous solution at 60° C. for 1 hour to hydrolyze the amido into carboxyl group.

Bovine vascular endothelial cells were cultured on the obtained film in the same manner as in Example 1. The cells selectively grew only on the polymer-grafted portion (exposed portion) to give a cell pattern.

EXAMPLE 7

A polyacrylamide-grafted polytetrafluoroethylene film was prepared in the same manner as in Example 6, and it was immersed in an aqueous NaOH alkaline solution of sodium hypochlorite and kept at 0° C. for 1 hours to convert the amido portion into amino group by means of Hofmann degradation.

Bovine vascular endothelial cells were cultured on the thus obtained film in the same manner as in Example 1. The cells selectively grew only in the polymer-grafted portion (exposed portion) to give a cell pattern.

In addition to the ingredients used in the examples, other ingredients can be used in the examples as set forth in the specification to obtain substantially the same results.

What we claim is:

1. A process for preparing a cell arrangement control device which consists essentially of applying a photosensitive, cell non-adhesive polymer to a cell adhesive surface, irradiating patternwise the resulting photosensitive cell non-adhesive polymer layer with a light, and developing the irradiated layer to leave the irradiated portion on said cell adhesive surface, thereby providing a pattern of said cell non-adhesive polymer on said cell adhesive surface.

2. The process of claim 1, wherein said photosensitive polymer is a cell non-adhesive polymer having at least one azido group.

3. The process of claim 1, wherein said photosensitive polymer is a composition containing a cell non-adhesive polymer and a compound having at least two azido groups.

* * * * *